(12) United States Patent
Tuo et al.

(10) Patent No.: US 10,406,084 B2
(45) Date of Patent: Sep. 10, 2019

(54) LOW REFRACTIVE INDEX, HIGH TRANSPARENCY, AND ABRASIVE TYPE SILICA, PREPARATION METHOD AND APPLICATION THEREOF

(71) Applicant: GUANGZHOU FEIXUE MATERIAL TECHNOLOGY CO ., LTD., Guangzhou (CN)

(72) Inventors: Wenxi Tuo, Guangzhou (CN); Yingguang Lin, Guangzhou (CN); Wenying Gao, Guangzhou (CN); Fei Hu, Guangzhou (CN); Canming Hou, Guangzhou (CN)

(73) Assignee: GUANGZHOU FEIXUE MATERIAL TECHNOLOGY CO., LTD., Guangzhou (CN)

(*) Notice: Subject to any disclaimer, the term of this patent is extended or adjusted under 35 U.S.C. 154(b) by 0 days.

(21) Appl. No.: 16/179,994

(22) Filed: Nov. 4, 2018

(65) Prior Publication Data

US 2019/0133901 A1    May 9, 2019

(30) Foreign Application Priority Data

Nov. 6, 2017  (CN) .......................... 2017 1 1080844

(51) Int. Cl.
  *A61K 8/25* (2006.01)
  *C01B 33/154* (2006.01)
  *A61Q 11/00* (2006.01)

(52) U.S. Cl.
  CPC ............... *A61K 8/25* (2013.01); *A61Q 11/00* (2013.01); *C01B 33/154* (2013.01)

(58) Field of Classification Search
  None
  See application file for complete search history.

(56) References Cited

U.S. PATENT DOCUMENTS

| | | | | |
|---|---|---|---|---|
| 4,040,858 | A * | 8/1977 | Wason ..................... | A61K 8/25 106/431 |
| 6,616,916 | B1 * | 9/2003 | Karpe ..................... | A61K 8/25 423/339 |
| 6,869,595 | B2 * | 3/2005 | Kostinko ................. | A61K 8/25 423/335 |
| 7,008,617 | B1 * | 3/2006 | Karpe ..................... | A61K 8/25 423/335 |
| 2003/0131536 | A1 * | 7/2003 | Kostinko ................. | A61K 8/25 51/308 |
| 2013/0284974 | A1 * | 10/2013 | Trabzuni ................. | C01B 33/32 252/182.32 |

FOREIGN PATENT DOCUMENTS

| | | | |
|---|---|---|---|
| CN | 1693193 | A * | 11/2005 |
| CN | 1693193 | A | 11/2005 |
| CN | 102530970 | A | 7/2012 |
| CN | 103449451 | A | 12/2013 |
| CN | 104030303 | A | 9/2014 |
| CN | 105712359 | A * | 6/2016 |
| CN | 105712359 | A | 6/2016 |

OTHER PUBLICATIONS

Google Patents. English Translation of CN 1693193 A. "Process for preparing silicon dioxide for green high transparent toothpaste." Obtained from https://patents.google.com/patent/CN1693193A/en?oq=CN+1301904 on Jan. 2, 2019, originally published in Chinese in 2005, 5 printed pages. (Year: 2005).*
Google Patents. English Translation of CN105712359A. "Abrasive silicon dioxide for low-abrasion high-cleaning-power toothpaste and preparation method thereof." Obtained from https://patents.google.com/patent/CN105712359A/en?oq=CN+105712359 on Jan. 3, 2019, 6 pages, originally published 2016. (Year: 2016).*
S Palaniandy, Kam Azizli, H Hussin, SFS Hashim. "Mechanochemistry of silica on jet milling." Journal of Materials Processing Technology, vol. 205, 2008, pp. 119-127. (Year: 2008).*
PQ Europe. "Sodium and Potassium Silicates." https://www.pqcorp.com/docs/default-source/recommnended-literature/pq-corporation/potassium-silicates/sodium-and-potassium-silicates-brochure-eng-oct-2004.pdf?sfvrsn=4f83aa6e_3 accessed Mar. 25, 2019, available Oct. 2004, pp. 1-16 (Year: 2004).*
Y Ding, G Yin, X Liao, Z Huang, X Chen, Y Yao. "Key role of sodium silicate modulus in synthesis of mesoporous silica SBA-15 rods with controllable lengths and diameters." Materials Letters, vol. 75, 2012, pp. 45-47. (Year: 2012).*
Grace Davison. "Sylodent/Syloblanc." Accessed at https://grace.com/personal-care/en-US/Documents/Sylodent_syloblanc_br_E_120126.pdf on May 1, 2019. Originally published 2011. pp. 1-12. (Year: 2011).*
JM Provis, A Kilcullen, P Duxson, DG Brice, JSJ van Deventer. "Stabilization of Low-Modulus Sodium Silicate Solutions by Alkali Substitution." Industrial & Engineering Chemistry Research, vol. 51, 2012, pp. 2483-2486. (Year: 2012).*

* cited by examiner

*Primary Examiner* — Isaac Shomer
(74) *Attorney, Agent, or Firm* — Gokalp Bayramoglu

(57) ABSTRACT

An abrasive type silica with low refractive index and high transparency, a preparation method and an application thereof are disclosed. The preparation method of the present invention includes the following steps: S1, a sodium sulfate solution is added into a reaction tank, the solution is heated to 80-95° C., a sodium silicate solution and a sulfuric acid solution are added at the same time while stirring, the dropping rate of the sodium silicate solution is controlled at 13-15 m³/h, the dropping rate of the sulfuric acid solution is controlled to ensure that the pH value of the reaction process is 3.0-4.5, and stirring is continued for 10-15 min after the adding is finished; and S2, the formed silica is filter pressed, washed, spray-dried and airflow crushed to prepare the abrasive type silica with low refractive index and high transparency.

13 Claims, No Drawings

LOW REFRACTIVE INDEX, HIGH TRANSPARENCY, AND ABRASIVE TYPE SILICA, PREPARATION METHOD AND APPLICATION THEREOF

CROSS REFERENCE TO RELATED APPLICATIONS

This application is based upon and claims priority to Chinese Patent Application No. 201711080844.1, filed on Nov. 6, 2017, the entire contents of which are incorporated herein by reference.

TECHNICAL FIELD

The present invention belongs to the technical field of silica, and particularly relates to an abrasive type silica with low refractive index and high transparency, a preparation method and an application thereof.

BACKGROUND

In recent years, transparent toothpastes have become well known oral cleaning products. At present, due to high chemical stability and good compatibility with various additives, silica is an essential raw material to produce the transparent toothpaste, and silica toothpaste is becoming more and more competitive in the market.

In order to make transparent toothpaste, it is necessary to make the refractive index of the liquid phase of toothpaste close to or even same as that of the solid phase. The liquid phase is composed mainly of water and humectant, sorbitol, polyethylene glycol and glycerin are commonly used humectants. In general, the refractive index of silica is in the range of 1.430-1.460, while the refractive index of 70% sorbitol is 1.457, the refractive indexes of water, polyethylene glycol, glycerol are 1.333, 1.46, and 1.47, respectively. The refractive index of a solution having a ratio of 70% sorbitol:water=90:10 is 1.4458, the refractive index of a solution having a ratio of 70% sorbitol:water=87.5:12.5 is 1.4390, the refractive index of a solution having a ratio of 70% sorbitol:water=85:15 is 1.4340, and the refractive index of a solution having a ratio of 70% sorbitol:water=80:20 is 1.4300. Through adjusting the ratio of humectant to water, it can make the refractive index of liquid phase coincide with that of the solid phase, thereby achieving the effect of transparency. In addition to the refractive index, the own transparency of the silica is also very important, generally the transparency of the silica requires more than 85%. As long as meeting the above two conditions at the same time, diffuse reflection will not occur, thereby better transparent toothpaste can be formed.

At present, the transparency of the silica with refractive index range of 1.440-1.460 can reach more than 90%, but the transparency of silica is lower than 80% in the low refractive index range of 1.430-1.440. In transparent toothpaste formulation, the water content is often low, normally about 10%, but the content of humectant such as sorbitol, polyethylene glycol or glycerin is about 65%, which leads to a high cost of the transparent toothpaste. Therefore, it is necessary to develop a new method to produce the silica with high transparency in the low refractive index, which can be used in a transparent toothpaste formulation to increase the content of water, while reducing the content of humectant, thereby reducing the production cost.

SUMMARY

In order to solve the problem that the existing dental type silica has low transparency in the low refractive index, the present invention provides a method to produce an abrasive type silica with high transparency in low refractive index. The process is simple and stable, the transparency of silica in the low refractive index range of 1.430-1.440 can be improved to more than 90%, while the transparency can reach more than 95% in the refractive index range of 1.440-1.460.

The present invention provides a preparation method of an abrasive type silica with low refractive index and high transparency, which includes the following steps:

S1, sodium sulfate solution with the volume of 11-13 $m^3$ is added into the reaction kettle, heating to 80-95° C., sodium silicate solution with the volume of 8.5-12 $m^3$ and sulfuric acid solution are titrated under stirring, the dropping rate of sodium silicate solution is in the range of 13-15 $m^3/h$, the dropping rate of sulfuric acid solution is controlled to ensure that the pH value of the reaction process is in the range of 3.0-4.5. Stirring is continued for 10-15 minutes after the addition is completed;

S2, the silica obtained in S1 is filtered, and washed, and the washed silica is spray-dried and jet milled to obtain an abrasive type silica with high transparency and low refractive index.

Further, the mass percentage of sodium sulfate solution is 6.5-8.5%.

Further, the sodium silicate solution has a modulus of 2.5-3.0, and a concentration of 1.5-3.0 M.

Further, the concentration of the sulfuric acid solution is 4.0-5.0 M.

Further, the stirring speed is 40-60 Hz.

Further, the salinity of washed silica is 1.8-2%.

In the preparation method of the present invention, the sodium sulfate is used as reaction promoter, and the sodium silicate is used for neutralization with sulfuric acid as raw material, and the concentration, temperature, pH value and other parameters are under control during the reaction process to obtain an abrasive type silica with low refractive index and high transparency.

The mechanism of the preparation method is as follows: sodium silicate is a complex polymer, polymerization and depolymerization reaction take place continually inside thereof. The dissociation products of sodium silicate aqueous solution contribute to the formation of average silicic acid, hexamethylene silicic acid, and silicic acid of the eight cubes and polysilicic acid with a branch with specific structure. The concentration of each component in the sodium silicate solution will change with the conditions such as pH value, concentration, temperature and salinity.

When the pH value is controlled in the range of 3.0-4.5 during the reaction process, and while the gel is formed, the particle size of primary gel is small, silica gel with a pore structure is easily formed when aggregated, the silica particles are more uniform in the secondary aggregation, helping to improve the transparency. The structure of formed silica is fluffier and the pore structure is more abundant under acidic conditions, helping to improve the transparency. But the amount of water and oil absorption of silica will rise under acidic conditions, so it is necessary to add sodium sulfate to precipitate silica rapidly through salting-out effect, meanwhile, increasing the reaction temperature to 80-95° C. could help accelerating the reaction rate, so that the silica obtain a high transparency and also a certain abrasive performance.

The conventional production of the silica made by the precipitation method often utilizes a solution of sodium silicate with a modulus of 3.3-3.45, although the transparency of the produced silica could reach more than 90%, the refractive index is in the range of 1.440-1.460 basically. While the inventors have found that in the experiment, the refractive index of silica produced under the same condition moves down with the decrease of modulus of sodium silicate, that is, the transparency of the produced silica with the refractive index not more than 1.440 gradually increases, however, when the modulus of sodium silicate is reduced to not more than 2.5, the transparency is not further improved, but rather tends to be lowered, at the same time, the product yield is lowered, which is detrimental to the product industrialization. Thus, the present invention uses the sodium silicate with modulus of 2.5-3.0, and more preferably of 2.8-3.0, through controlling the pH value and the reaction temperature during reaction process, the number of hydroxyl groups on the surface of the silica is increased to obtain a high transparency product with low refractive index.

After the reaction, the washed silica is spray-dried to make the particle size of product more uniform and the pore structure more abundant. At the same time, the salinity is controlled in the range of 1.8-2.0% when washed to achieve the viscosity increasing when applied in toothpaste under the same physical and chemical indices, and to lower the water loss of the toothpaste, thus being able to maintain high transparency for a long time.

Accordingly, the present invention also provides the abrasive type silica with low refractive index and high transparency prepared by the above method and its application in the toothpaste. The transparency of this silica in the refractive index range of 1.430-1.440 reaches up to 90% or more, the transparency of the silica with refractive index range of 1.440-1.460 can reach more than 95%, meanwhile water absorption thereof is 16-22 ml/20 g, and oil absorption thereof is 90-130 ml/100 g, apparent density thereof is equal to or more than 0. 3 g/mL, meeting the standard requirements of an abrasive type silica. Applying the silica to the toothpaste, in particular to a transparent toothpaste formulation, can increase the amount of water usage and reduce the amount of humectant, thereby reducing the production costs.

Therefore, the present invention has the following advantages compared to the prior art:

First, the abrasive type silica with low refractive index and high transparency provided by the present invention has simple manufacturing method, stable process, controllable conditions, low production cost and low environmental pollution, industrialized production can be achieved, and transparency of silica in low refractive index can be effectively improved.

Second, the transparency of the silica with refractive index range of 1.430-1.440 can reach more than 90%, and the transparency is higher than 95% with the refractive index range of 1.440-1.460, meanwhile water absorption thereof is 16-22 ml/20 g, oil absorption thereof is 90-130 ml/100 g, and apparent density thereof is equal to or more than 0. 3 g/mL, high transparency and good abrasion resistance in low refractive index are presented.

Finally, the silica of the present invention can be applied to the toothpaste, in particular to a transparent toothpaste, which increases the amount of water usage, and reduces the amount of humectant, thereby greatly reducing the production cost of the toothpaste, and improving the profitability.

DETAILED DESCRIPTION

The present invention is described in detail below with reference to some specific embodiments, herein, schematic embodiments and illustrations are used for explaining the present invention, but are not intended to limit the present invention.

Embodiment I

Abrasive type silica with low refractive index and high transparency of the present invention and preparation method thereof.

S1, 11 $m^3$ sodium sulfate solution having a mass concentration of 6.5% was added to the reaction tank, the reaction tank was heated to 80° C., stirring at the stirring rate of 40 Hz, 8.5 $m^3$ sodium silicate solution with a concentration of 1.5 M and a modulus of 2.5, and sulfuric acid solution with a concentration of 4.0 M were dropped into the reaction tank at the same time, the dropping rate of sodium silicate solution was controlled at 13 $m^3$/h, and the dropping rate of sulfuric acid solution was controlled to ensure the pH value was 3.0 during the reaction, stirring was continued for 10 min after the addition was completed;

S2, the silica obtained in S1 was filtered, and washed, and the washed silica was spray-dried, and jet milled to obtain abrasive type silica with low refractive index and high transparency. Wherein, the salinity of the washed silica was 1.8%.

Embodiment II

Abrasive type silica with low refractive index and high transparency of the present invention and preparation method thereof.

S1, 13 $m^3$ sodium sulfate solution having a mass concentration of 8.5% was added to the reaction tank, the reaction tank is heated to 95° C., stirring at the stirring rate of 60 Hz, 12 $m^3$ sodium silicate solution with a concentration of 3.0 M and a modulus of 2.6, and sulfuric acid solution with a concentration of 5.0 M were dropped into the reaction tank at the same time, the dropping rate of sodium silicate solution was controlled at 15 $m^3$/h, and the dropping rate of sulfuric acid solution was controlled to ensure the pH value was 4.5 during the reaction, stirring was continued for 15 min after the addition was completed;

S2, the silica obtained in S1 was filtered, and washed, and the washed silica was spray-dried, and jet milled to obtain abrasive type silica with low refractive index and high transparency. Wherein, the salinity of the washed silica was 2.0%.

Embodiment III

Abrasive type silica with low refractive index and high transparency of the present invention and preparation method thereof.

S1, 12 $m^3$ sodium sulfate solution having a mass concentration of 7.0% was added to the reaction tank, the reaction tank is heated to 85° C., stirring at the stirring rate of 50 Hz, 10 $m^3$ sodium silicate solution with a concentration of 2.0 M and a modulus of 2.8, and sulfuric acid solution with a concentration of 4.5 M were dropped into the reaction tank at the same time, the dropping rate of sodium silicate solution was controlled at 14 $m^3$/h, and the dropping rate of sulfuric acid solution was controlled to ensure the pH value was 4.0 during the reaction, stirring was continued for 10 min after the addition was completed;

S2, the silica obtained in S1 was filtered, and washed, and the washed silica was spray-dried, and jet milled to obtain abrasive type silica with low refractive index and high transparency. Wherein, the salinity of the washed silica was 1.8%.

Embodiment IV

Abrasive type silica with low refractive index and high transparency of the present invention and its preparation method:

S1, 13 m$^3$ sodium sulfate solution having a mass concentration of 8.0% was added to the reaction tank, the reaction tank is heated to 80° C., stirring at the stirring rate of 60 Hz, 12 m$^3$ sodium silicate solution with a concentration of 1.5 M and a modulus of 3.0, and sulfuric acid solution with a concentration of 5.0 M were dropped into the reaction tank at the same time, the dropping rate of sodium silicate solution was controlled at 14 m$^3$/h, and the dropping rate of sulfuric acid solution was controlled to ensure the pH value was 4.0 during the reaction, stirring was continued for 10 min after the addition was completed;

S2, the silica obtained in S1 was filtered, and washed, and the washed silica was spray-dried, and jet milled to obtain abrasive type silica with low refractive index and high transparency. Wherein, the salinity of the washed silica was 1.9%.

Embodiment V

Abrasive type silica with low refractive index and high transparency of the present invention and preparation method thereof.

S1, 12 m$^3$ sodium sulfate solution having a mass concentration of 6.5% was added to the reaction tank, the reaction tank is heated to 90° C., stirring at the stirring rate of 40 Hz, 11 m$^3$ sodium silicate solution with a concentration of 3.0 M and a modulus of 2.8, and sulfuric acid solution with a concentration of 4.0 M were dropped into the tank at the same time, the dropping rate of sodium silicate solution was controlled at 15 m$^3$/h, and the dropping rate of sulfuric acid solution was controlled to ensure the pH value was 3.5 during the reaction, stirring was continued for 15 min after the addition was completed;

S2, the silica obtained in S1 was filtered, and washed, and the washed silica was spray-dried, and jet milled to obtain abrasive type silica with low refractive index and high transparency. Wherein, the salinity of washed silica was 2.0%.

Embodiment VI

The application of the abrasive type silica with low refractive index and high transparency of this invention in toothpaste.

The abrasive type silica with low refractive index and high transparency of the embodiment I-V were applied to toothpaste and toothpastes 1-5 were prepared respectively. The specific formulation of the toothpastes was as follows (% by mass): abrasive type silica was 18%, silica thickener type was 3%, sorbitol was 55%, polyethylene glycol was 4%, carboxymethyl cellulose was 0.6%, carrageenan was 0.4%, saccharin was 0.2%, sodium benzoate was 0.2%, flavor was 1%, sodium dodecyl sulfate was 2%, and water was 15.6%.

The toothpaste was detected according to the toothpaste standard GB8372, the paste was smooth with exquisite appearance, and crystal clear, transparency was high, pH value was 7.5, consistency was 12 mm, the results of main testing index meet the requirements of the toothpaste standard.

Wherein, the perspective degree of the toothpastes is shown in the following table:

| Toothpastes | Transparency | | | | |
| --- | --- | --- | --- | --- | --- |
| | 1.0 mm | 0.5 mm | 0.1 mm | 0.05 mm | 0.01 mm |
| 1 | Clearly visible | Clearly visible | Clearly visible | Clearly visible | Visible |
| 2 | Clearly visible | Clearly visible | Clearly visible | Clearly visible | Visible |
| 3 | Clearly visible | Clearly visible | Clearly visible | Clearly visible | Visible |
| 4 | Clearly visible | Clearly visible | Clearly visible | Clearly visible | Visible |
| 5 | Clearly visible | Clearly visible | Clearly visible | Clearly visible | Visible |

Comparative Example I

As compared with the embodiment III, the present comparative example differs only in that: a sodium silicate solution has a modulus of 2.0.

Comparative Example II

As compared with the embodiment III, the present comparative example differs only in that: a sodium silicate solution has a modulus of 3.3.

Comparative Example III

As compared with the embodiment III, the present comparative example differs only in that: pH value of the reaction procedure is controlled at 2.5.

Comparative Example IV

As compared with the embodiment III, the present comparative example differs only in that: pH value of the reaction process is controlled at 5.0.

Comparative Example V

As compared with the embodiment III, the present comparative example differs only in that: the reaction temperature is controlled at 70° C.

Comparative Example VI

As compared with the embodiment III, the present comparative example differs only that: the reaction temperature is controlled at 100° C.

Test Case I

Performance test of the abrasive type silica with low refractive index and high transparency of the present invention.

Transparency, amount of water absorption and oil absorption, and apparent density of the silica prepared by the embodiments 1-5 and comparative examples 1-6 were detected in a refractive index range of 1.430-1.460, the results are shown in Table 1.

TABLE 1

The detection results of each silica

| Item | Light transmittance/Transparency (%) | | | | | | Water absorption amount mL/20 g | Oil absorption amount mL/100 g | Apparent density g/mL |
|---|---|---|---|---|---|---|---|---|---|
| | 1.430 | 1.435 | 1.438 | 1.440 | 1.443 | 1.450 | | | |
| Embodiment I | 74.1 | 82.3 | 92.0 | 97.5 | 97.1 | 91.0 | 22.0 | 130 | 0.30 |
| Embodiment II | 70.4 | 80.0 | 91.2 | 91.7 | 95.0 | 90.4 | 16.0 | 90 | 0.50 |
| Embodiment III | 77.5 | 86.2 | 94.4 | 97.5 | 97.8 | 92.0 | 18.5 | 105 | 0.39 |
| Embodiment IV | 71.9 | 80.7 | 91.5 | 94.4 | 95.8 | 89.5 | 17.8 | 98 | 0.45 |
| Embodiment V | 72.3 | 80.2 | 91.5 | 94.7 | 95.4 | 88.6 | 19.0 | 108 | 0.37 |
| Comparative Example I | 59.4 | 63.0 | 86.0 | 90.7 | 91.1 | 70.4 | 19.1 | 108 | 0.37 |
| Comparative Example II | 72.4 | 76.9 | 80.5 | 92.5 | 90.1 | 80.9 | 18.0 | 100 | 0.4 |
| Comparative Example III | 87.4 | 89.0 | 92.3 | 94.6 | 97.5 | 95.5 | 30.0 | 162 | 0.28 |
| Comparative Example IV | 64.1 | 77.3 | 84.0 | 89.3 | 91.4 | 84.3 | 18.5 | 105 | 0.39 |
| Comparative Example V | 73.0 | 85.5 | 87.9 | 90.8 | 91.2 | 90.4 | 29.3 | 150 | 0.27 |
| Comparative Example VI | 77.0 | 82.1 | 92.2 | 95.3 | 89.0 | 87.6 | 16.8 | 94 | 0.48 |

As can be seen from Table 1:

(1) the transparency of the silica of embodiments 1-5 in refractive index range of 1.430-1.440 can reach more than 90%, and is higher than 95% in the refractive index range of 1.440-1.460, having high transparency in the low refractive index. Meanwhile, water absorption of the silica of the present invention is 16-22 ml/20 g, oil absorption is 90-130 ml/100 g, and apparent density is equal to or more than 0.3 g/mL, meeting the standard requirements of abrasive type silica, and it has good abrasive properties, suitable for use in toothpaste.

(2) As compared with the embodiment III, Comparative Example I and Comparative Example II respectively decreases and increases the modulus of sodium silicate solution, thereby the transparency of the silica is found to have a significantly reduce.

(3) As compared with the embodiment III, Comparative Example III reduces the pH value in the reaction process, the transparency of the silica is enhanced, but significant increases of the amount of water absorption and oil absorption are observed, abrasive performance of the silica is reduced, and property thereof is inclined to silica thickener type, which does not meet the standard of abrasive silica; in the Comparative Example IV, the pH value of the reaction process is increased, thus there is a significant reduction in the transparency of the silica.

(4) As compared with the embodiment III, Comparative Example V reduces the reaction temperature, there is a significant decrease in the transparency of the silica, and the water absorption and oil absorption are significantly increased, the abrasive performance is reduced, which does not meet the standard of abrasive silica; Comparative Example VI enhances the reaction temperature, but the transparency of the silica is not increased, rather reduced.

Test Case II

Application effect of the abrasive type silica with low refractive index and high transparency of the present invention in the toothpaste Specific toothpaste formulations are shown below in Table 2:

TABLE 2

| Ingredients of toothpaste/% | Toothpaste A | Toothpaste B | Toothpaste C | Toothpaste D |
|---|---|---|---|---|
| Abrasive type silica | 18(silica of embodiment III) | 18(silica of embodiment III) | 18(silica of embodiment III) | 18(silica of comparative example II) |
| Thickening type silica | 3 | 3 | 3 | 3 |
| Sorbitol | 59 | 57 | 55 | 55 |
| Polyethylene glycol | 4 | 4 | 4 | 4 |
| Carboxymethyl cellulose | 0.6 | 0.6 | 0.6 | 0.6 |
| Carrageenan | 0.4 | 0.4 | 0.4 | 0.4 |
| Saccharin | 0.2 | 0.2 | 0.2 | 0.2 |
| Sodium benzoate | 0.2 | 0.2 | 0.2 | 0.2 |
| Essence | 1 | 1 | 1 | 1 |
| Sodium lauryl sulfate | 2 | 2 | 2 | 2 |
| Water | 11.6(liquid phase 1.438) | 13.6(liquid phase 1.435) | 15.6(liquid phase 1.430) | 15.6(liquid phase 1.430) |

The degree of transparency of the above-mentioned toothpastes are detected, results are shown in the following Table 3:

TABLE 3

Perspective Degree of the Toothpaste

| Toothpaste | Transparency | | | | | |
|---|---|---|---|---|---|---|
| | 2 mm | 1.0 mm | 0.5 mm | 0.1 mm | 0.05 mm | 0.01 mm |
| Toothpaste A | Clearly visible | Clearly visible | Clearly visible | Clearly visible | Clearly visible | Clearly visible |

TABLE 3-continued

Perspective Degree of the Toothpaste

| Tooth- | Transparency | | | | | |
|---|---|---|---|---|---|---|
| paste | 2 mm | 1.0 mm | 0.5 mm | 0.1 mm | 0.05 mm | 0.01 mm |
| Tooth-paste B | Clearly visible | Clearly visible | Clearly visible | Clearly visible | Clearly visible | Clearly visible |
| Tooth-paste C | Clearly visible | Clearly visible | Clearly visible | Clearly visible | Clearly visible | Visible |
| Tooth-paste D | Visible | Visible | Fuzzy | Very fuzzy | Very fuzzy | Very fuzzy |

As can be seen in the table above: when silica of the present invention is applied to the toothpaste, the transparent performance of the toothpaste is good, the paste is crystal clear, and the perspective degree is high. Wherein, when applying to toothpaste with a water content of 15.6%, the paste remains clear, increasing the amount of water used in the toothpaste and reducing the amount of humectant by 4%. Thus, when the silica of the present invention is applied to the toothpaste, for toothpaste formulation having high transparency requirement, 4% more of water can be added, and for the semi-transparent toothpaste, it is possible to add 4-10% more of water, thus greatly reducing the production cost of the toothpaste.

The above embodiments only schematically explain the principle and efficacy of the present invention, rather than limit the invention. Any person familiar with the technology may modify or alter the above embodiments without prejudice to the spirit and scope of the present invention. Therefore, all equivalent modifications or changes made by persons of ordinary skill in the art without departing from the spirit and technical thoughts disclosed by the present invention shall still be covered by the claims of the present invention.

What is claimed is:

1. A method of preparing an abrasive type silica consisting of the following steps:

S1: adding 11-13 m$^3$ sodium sulfate solution to a reaction kettle, heating the sodium sulfate solution to 85° C., stirring and titrating the sodium sulfate solution with 8.5-12 m$^3$ sodium silicate solution with a concentration of 1.5-3.0 M and a modulus of 2.8 and a sulfuric acid solution to obtain a mixed solution, controlling the dropping rate of the sodium silicate solution at 13-15 m$^3$/h, controlling the dropping rate of the sulfuric acid solution to ensure that the pH value of the reaction process is 4.0, and stirring the mixed solution for 10-15 min after addition of the sodium silicate solution and addition of the sulfuric acid solution were completed to obtain a silica;

S2: filtering the silica, washing the filtered silica to obtain a washed silica, spray-drying, and jet-milling the washed silica to obtain abrasive type silica;

S3: optionally adding the abrasive silica to toothpaste;

wherein the abrasive silica has a light transmittance of 91.5-94.4% at a refractive index of 1.438.

2. The method of claim 1, wherein the mass concentration of the sodium sulfate solution is 6.5-8.5%.

3. The method of claim 1, wherein the concentration of the sulfuric acid solution is 4.5-5.0 M.

4. The method of claim 1, wherein the salinity of the washed silica is 1.8-2%.

5. The method of claim 1, wherein the abrasive silica has a light transmittance of 70.4-77.5% at a refractive index of 1.430.

6. The method of claim 1, wherein the abrasive silica has a light transmittance of 80.0-86.2% at a refractive index of 1.435.

7. The method of claim 1, wherein the abrasive silica has a light transmittance of 94.4-97.5% at a refractive index of 1.440.

8. The method of claim 1, wherein the abrasive silica has a light transmittance of 95.4-97.8% at a refractive index of 1.443.

9. The method of claim 1, wherein the abrasive silica has a light transmittance of 88.6-92.0% at a refractive index of 1.450.

10. The method of claim 1, wherein the abrasive silica has a water absorption amount of 16.0-22.0 mL/20 g.

11. The method of claim 1, wherein the abrasive silica has an oil absorption of 90-130 mL/100 g.

12. The method of claim 1, wherein the abrasive silica has an oil absorption of 90-105 mL/100 g.

13. The method of claim 1, wherein the abrasive silica has an apparent density of 0.30-0.50 g/mL.

* * * * *